US00PP26206P2

(12) United States Plant Patent
Miklósné

(10) Patent No.: US PP26,206 P2
(45) Date of Patent: Dec. 15, 2015

(54) ***PRUNUS* PLANT NAMED 'ZITA'**

(50) Latin Name: *Prunus laurocerasus*
Varietal Denomination: Zita

(71) Applicant: Józsa Miklósné, Szombathely (HU)

(72) Inventor: Józsa Miklósné, Szombathely (HU)

( * ) Notice: Subject to any disclaimer, the term of this patent is extended or adjusted under 35 U.S.C. 154(b) by 0 days.

(21) Appl. No.: 13/986,511

(22) Filed: May 9, 2013

Related U.S. Application Data

(60) Provisional application No. 61/797,658, filed on Dec. 12, 2012.

(51) Int. Cl.
*A01H 5/12* (2006.01)

(52) U.S. Cl.
USPC ..... Plt./180

(58) Field of Classification Search
USPC ..... Plt./180
See application file for complete search history.

(56) References Cited

PUBLICATIONS http://www.gabot.de/index.php/Details-Plantarium-2012/540/0/?&no_cache=1&tx_ttnews%5Btt_news%5D=218168&cHash=acf69d78726831af6d9f58fce270049e, Gabot Dossier: Plantarium 2012, published Aug. 26, 2011, article on *Prunus laurocerasus* 'Zita'.* www.esveld.nl/htmldia/p/prlzit.htm, Plantentuin Esveld, published Aug. 24, 2011, *Prunus laurocerasus* 'Zita', with embedded link to sale page www.esveld.nl/plant.php?plant=Prunus%20laurocerasus%20%277Za%27&taal=en.*

* cited by examiner

*Primary Examiner* — Anne Grunberg
(74) *Attorney, Agent, or Firm* — Penny J. Aguirre

(57) ABSTRACT

A new cultivar of *Prunus laurocerasus*, 'Zita', characterized by its dark green glossy mature leaves and young leaves that are bronze red, its bushy spreading mounded plant habit; reaching about 0.8 m in height and 2 m in width, its slow growth rate, its good disease resistance, and its hardiness at least in U.S.D.A. Zones 6 to 9.

2 Drawing Sheets

Botanical classification: *Prunus laurocerasus.*
Variety denomination: 'Zita'.

BACKGROUND OF THE INVENTION

The present invention relates to a new and distinct cultivar of *Prunus laurocerasus*, and will be referred to hereafter by its cultivar name, 'Zita'. 'Zita' is a new cultivar of cherry laurel grown for use as a landscape plant.

The new cultivar of *Prunus*, 'Zita', arose from an ongoing breeding program by the Inventor in Szombathely, Hungary. The new cultivar was selected as a naturally occurring whole plant mutation in summer of 2002 that arose from seeds collected, pooled and sown from open pollination of the cultivars 'Mari', 'Piri', and Klàri (all three not patented). The exact parenage is unknown.

Asexual propagation of the new cultivar was first accomplished by stem cuttings by the Inventor in Szombathely, Hungary in September of 2002. Asexual propagation by stem cuttings has determined that the characteristics of the new cultivar are stable and reproduced true to type in successive generations.

SUMMARY OF THE INVENTION

The following traits have been repeatedly observed and represent the characteristics of the new *Prunus*. These attributes in combination distinguish 'Zita' as a unique-cultivar of *Prunus*.

1. 'Zita' exhibits dark green glossy mature leaves and young leaves that are bronze red in color.

2. 'Zita' exhibits a bushy spreading mounded plant habit; reaching about 0.8 m in height and 2 m in width.
3. 'Zita' exhibits exhibits a slow growth rate.
4. 'Zita' exhibits good disease resistance.
5. 'Zita' exhibits good hardiness with hardiness at least in U.S.D.A. Zones 6 to 9.

'Zita' is unique and unlike any other cultivars of *Prunus laurocerasus* known to the Inventor. Possible parent plants; 'Mari', 'Piri', and 'Klàri', all differ from 'Zita' in having young foliage that is green in color, in lacking glossy leaves, and in having a more vigorous growth rate. 'Zita' can be most closely compared to the cultivars 'Anbri' (not patented) and 'Otto Luyken' (not patented). 'Anbri' is similar to 'Zita' in foliage coloration, however 'Anbri' differs from 'Zita' in having leaves that are less elongated and larger and in having a more vigorous growth habit. 'Otto Luyken' is similar to 'Zita' in having glossy dark green mature leaves, but differs from 'Zita' in having young leaves that are green in color, a plant habit that is less dense and in not being as realiably cold hardy when grown under the same conditions.

BRIEF DESCRIPTION OF THE DRAWING

The accompanying, colored photographs illustrate the overall appearance and distinct characteristics of the new cultivar. The photographs were taken of a 5 year-old plants as grown outdoors in a trial bed in Szombathely, Hungary.

The photograph in FIG. 1 provides a vew of a row of plants of 'Zita'.

Figure 1:
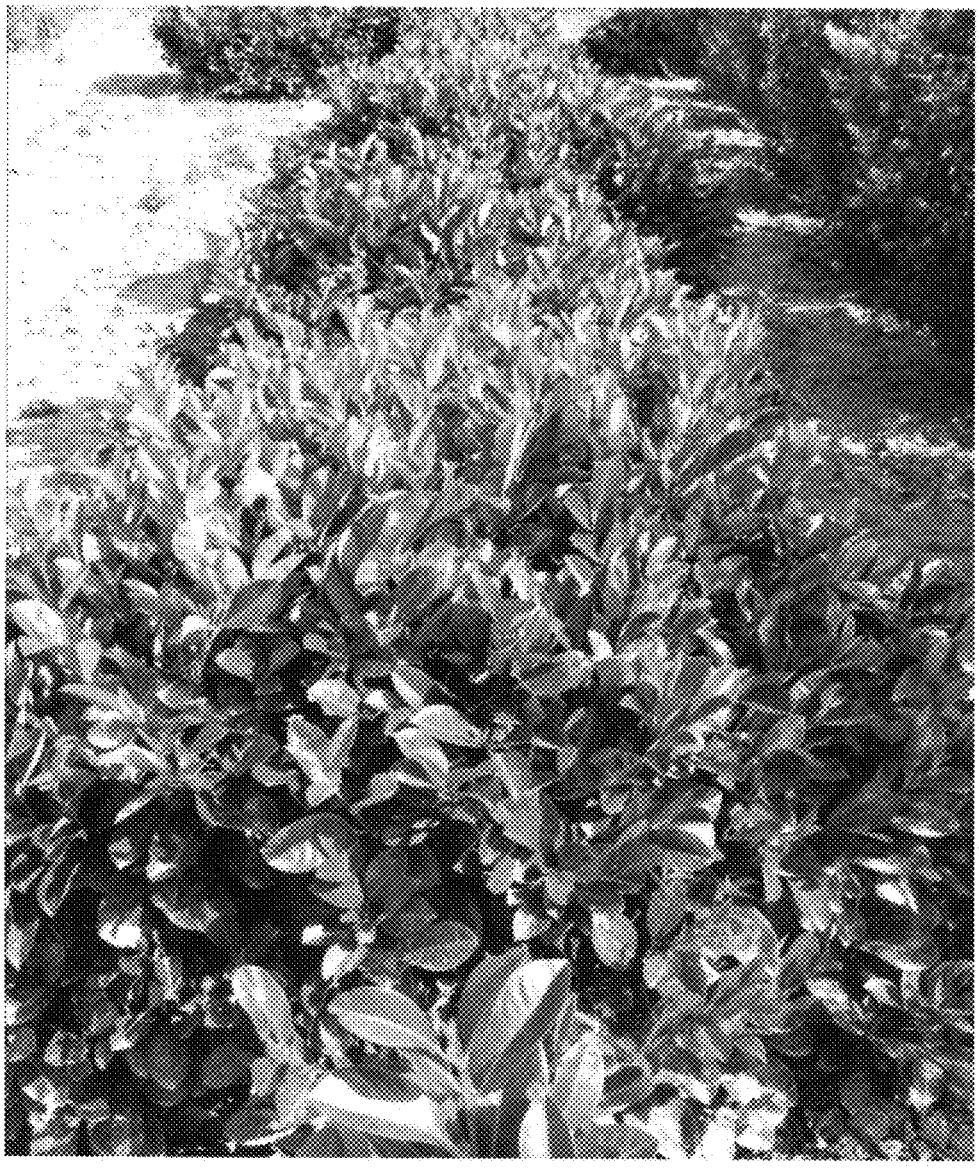
Figure 2:
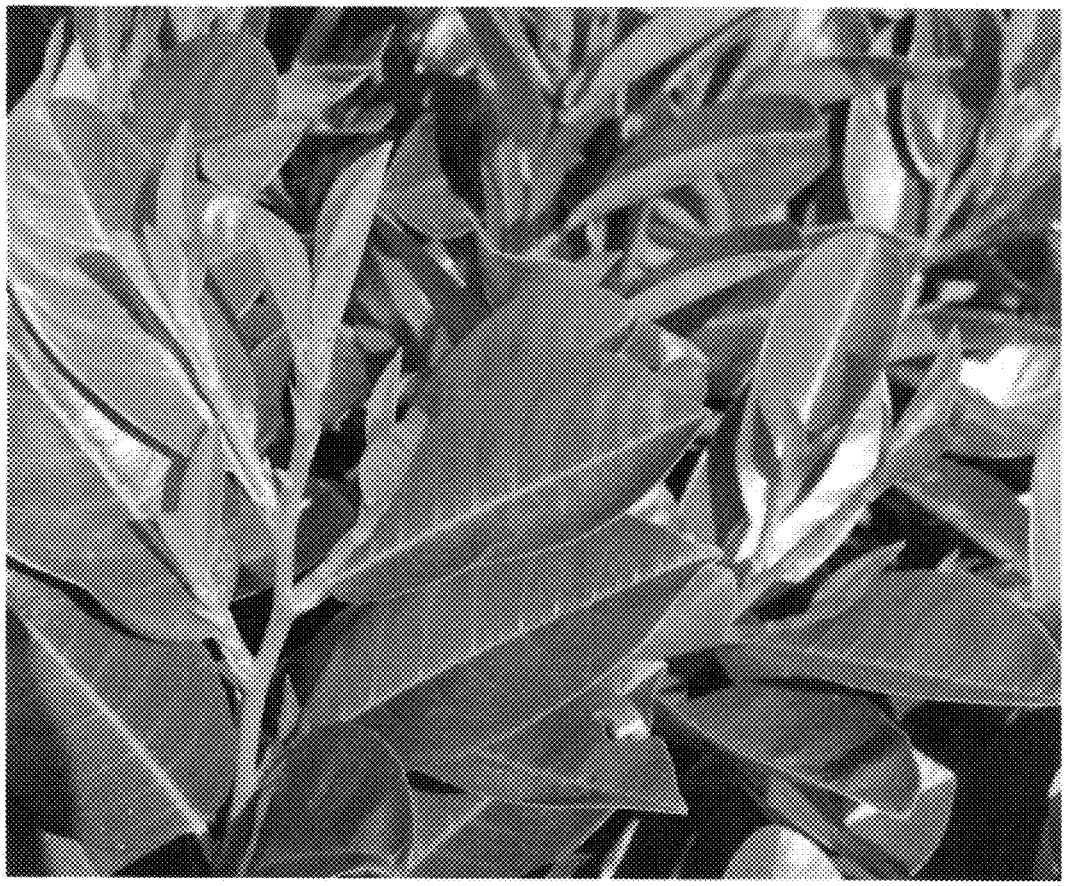

The photograph in FIG. 2 is a close-up view of young and mature leaves of 'Zita'.

The colors in the photographs are as close as possible with the digital photography techniques available, the color values cited in the detailed botanical description accurately describe the colors of the *Prunus*.

DETAILED BOTANICAL DESCRIPTION

The following is a detailed description of 10 year-old trees of the new cultivar as grown outdoors in a trial bed in Szombathely, Hungary. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen shrub.

*Plant habit*.—Spreading and mounded.

*Height and spread*.—Reaches about 2 m in width and about 0.8 m height.

*Hardiness*.—At least in U.S.D.A. Zones 6 to 9.

*Diseases and pests*.—Has been shown to have good resistance to mildew, leaf spot.

*Root description*.—Fleshy.

*Propagation*.—Stem cuttings.

*Root initiation*.—4 to 6 weeks in a greenhouse in autumn.

*Root development*.—Autumn rooted cuttings are overwintered in a greenhouse and potted in the spring after which they fully develop in a liner in 45 days at 20° to 25° C. during the summer.

*Growth rate*.—Slow.

Stem description:

*Shape*.—Slightly oval.

*Stem color*.—New growth; slightly lighter than N144B and slightly suffused in areas with 172B, mature growth; a blend of 145B and 144C, mature wood; N199B.

*Branching*.—4 to 6 main stems and 6 to 8 lateral braches per main stem with an average angle of 30° to 35 °.

*Stem size*.—Main stems; average of 0.8 m in length and 3 to 4 cm in diameter, lateral branches range from 10 to 50 cm in length and 0.5 to 1 cm in diameter.

*Stem surface*.—Young stems glabrous with slight glossy, mature stems dull.

*Branch internode length*.—Average of 4 cm.

*Stem fragrance*.—Emit a cherry aroma if bruised.

Foliage description:

*Leaf shape*.—Elongated elliptic.

*Leaf division*.—Simple.

*Leaf base*.—Cuneate.

*Leaf apex*.—Acute to cuspidate.

*Leaf fragrance*.—None.

*Leaf venation*.—Pinnate, conspicuously recessed on upper surface, color on mature leaves upper surface green, color of mature leaves lower surface green.

*Leaf margins*.—Entire.

*Leaf arrangement*.—Alternate.

*Leaf attachment*.—Petiolate.

*Leaf surface*.—Glabrous and highly glossy on upper surface and lower surface.

*Leaf size*.—Mature leaves range from 5 to 7 cm in length and an average 3 cm in width.

*Leaf internodes*.—Average of 2 cm.

*Leaf color*.—Newly expanded leaves upper and lower surface; 167A to 167B, mature leaves upper and lower surface; a blend of 144A and 144B and then changing to 137B.

*Petioles*.—Average of 0.5 cm in length and 2 mm in width, slightly lighter than N144B in color, glabrous surface.

Inflorescence description: Blooms have not been observed on the new cultivar.

It is claimed:

1. A new and distinct cultivar of *Prunus* plant named 'Zita' as herein illustrated and described.

* * * * *